United States Patent

Thomspon et al.

[11] Patent Number: 5,718,912
[45] Date of Patent: Feb. 17, 1998

[54] MUSCARINE AGONISTS

[75] Inventors: Wayne J. Thomspon; Pierre Mallorga, both of Lansdale; Richard W. Ransom, New Britain; Ian M. Bell, Harleysville; Michael F. Sugrue, Blue Bell; Peter M. Munson, Harleysville, all of Pa.

[73] Assignee: Merck & Co., Inc., Rahway, N.J.

[21] Appl. No.: 736,705

[22] Filed: Oct. 28, 1996

[51] Int. Cl.$^6$ ............... A61F 2/00; A01N 43/40; A61K 31/445
[52] U.S. Cl. ............... 424/427; 514/318; 514/323; 540/519; 546/199; 546/194; 546/193; 544/333
[58] Field of Search ............... 514/318, 323; 546/199, 194, 193; 544/333

[56] References Cited

U.S. PATENT DOCUMENTS 5,574,044  11/1996  Thompson ............... 514/316
5,591,708  1/1997  Richter ............... 510/463
5,591,890  1/1997  Jacobson ............... 562/412

OTHER PUBLICATIONS

R. Feifel, et al., *Br. J. Pharmacol*, 99, pp. 455–460 (1990).

F. Dorje, et al., *J. Pharmacol. and Exp. Thera.*, 256(2), pp. 727–733 (1991).

*Primary Examiner*—Joseph L. Schofer
*Assistant Examiner*—D. Faulkner
*Attorney, Agent, or Firm*—Sylvia A. Ayler; Mark R. Daniel

[57] ABSTRACT

This invention is concerned with novel 1-[cycloalkylpioeridin-4-yl]-2H benzimidazolones, their compositions and method of use. The novel compounds are selective muscarinic agonists of the m2 subtype with low activity at the m3 subtype. The compounds are effective for the treatment of glaucoma with fewer side effects than the pilocarpine therapy.

19 Claims, No Drawings

MUSCARINE AGONISTS

BACKGROUND OF THE INVENTION

Glaucoma is an ocular disorder associated with elavated intraocular pressures which are too high for normal function and may result in irreversible loss of visual function. If untreated, glaucoma may eventually lead to blindness. Ocular hypertension, i.e., the condition of elevated intraocular pressure without optic nerve head damage or characteristic glaucomatous visual field defects, is now believed by many ophthalmologists to represent the earliest phase of glaucoma.

Many of the drugs formerly used to treat glaucoma proved not entirely satisfactory. Only recently have clinicians noted that many β-adrenergic blocking agents are effective in reducing intraocular pressure. While many of these agents are effective in reducing intraocular pressure, they also have other characteristics, e.g. membrane stabilizing activity, that are not acceptable for chronic ocular use. Other agents which are used for treatment of glaucoma include carbonic anhydrase inhibitors and prostaglandins. Carbonic anydrase inhibitors work by blockade of inflow into the eye. Prostaglandins exert a reduction of scleral outflow. To date, only muscarinic agents work by directly increasing outflow. Since glaucoma is considered to be a result of decreased outflow from the eye, this approach provides greater therapeutic benefit by the nature of more direct action.

There have been recent advances made in the understanding of the cholinergic nervous system and the receptors thereto. Cholinergic receptors are proteins embedded in the wall of a cell that respond to the chemical acetylcholine. Particularly, it is now known that the cholinergic receptors are subdivided into nicotinic and muscarinic receptors and that the muscarinic receptors are not all of the same type. Recent literature indicates that there are at least five types of cholinergic muscarinic receptors (types m1 through m5). Receptors of type m1 are those present in abundance and thought to be enriched in the brain neural tissue and neural ganglia. The other receptors are concentrated in other tissues such as the heart, smooth muscle tissue or glands. While many pharmacological agents interacting with muscarinic receptors influence several types of receptors, some agents are known to have a major effect on a single type of receptor with relative selectivity. Still other agents may have a significant effect on more than one or even all types of receptors. For example, there is strong evidence that the receptors in the back of the eye responsible for outflow are comprised of the m2 and m3 subclass.

Topical administration of muscarinic agonist, pilocarpine, lowers intraocular pressure by increasing outflow. However, pilocarpine is a non-selective agonist, interacting with muscarinic receptors of several types. Additionally, the side effects associated with pilocarpine are miosis (decrease of pupil size) and systemic CNS effects which limit usefulness.

It is therefore an object of this invention to develop compounds which exhibit few side effects by selectively interacting with a muscarinic receptor.

SUMMARY OF THE INVENTION

This invention is concerned with novel 1-[cycloalkylpioeridin-4-yl]-2H benzimidazolones, their compositions and method of use. The novel compounds are selective muscarinic agonists of the m2 subtype with low activity at the m3 subtype. The compounds have good ocular penetration (bioavailability) when dosed at 0.1% to 15% by weight of medicament, especially about 0.5 to 2% by weight of medicament and are effective for the treatment and/or prevention of glaucoma with fewer side effects than the pilocarpine therapy, due to lower activity at the m3 subclass of muscarinic receptors.

DETAILED DESCRIPTION OF THE INVENTION

The novel compounds of this invention are represented by the structural formula I:

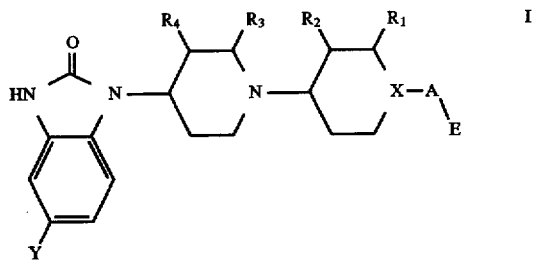

or pharmaceutically acceptable salts thereof, or diastereomers, enantiomers or mixtures thereof;
wherein:

$R_1$–$R_4$ are independently H, alkyl, halo, alkoxy, OH, HOCH2—, aryl, 3-pyridyl, 5-pyrimidinyl, amino, dialkylamino, alkene, thioalkyl, or alkylamino;

X is C or N;

A is alkyl, alkoxy, carboxyalkyl, alkoxyamino, alkylamino, dialkylamino, dialkoxyamino, carboxylic acid, =O, hydroxy, C=O, N, or does not exist;

E is H, alkyl, alkylamino, dialkylamino, aryl, heteroaryl, heterocycle, alkoxy, alkoxyaryl, carbonyl heterocycle, alkoxyheteroaryl, alkoxyheterocycle, or does not exist; and Y is H, alkyl, halo, alkylamino, alkoxyamino, alkoxy, dialkylamino, or amino.

The term heterocycle or heterocyclic, as used herein except where noted, represents a stable 5- to 7- membered monocyclic heterocyclic ting, which is either saturated or unsaturated, and which consists of carbon atoms and from one to three heteroatoms selected from the group consisting of N, O and S, and including any bicyclic group in which any of the above defined heterocyclic rings is fused to a benzene ring. The heterocyclic ring may be attached at any heteroatom or carbon atom which results in the creation of a stable structure. Examples of such heterocyclic rings include pyridine, pyrazine, pyrimidine, pyridazine, triazine, imidazole, pyrazole, triazole, quinoline, isoquinoline, quinazoline, quinoxaline, phthalazine, oxazole, isoxazole, thiazole, isothiazole, thiadiazole, oxadiazole, pyrrole, furan, thiophene, hydrogenated derivatives of these heterocyles such as piperidine, pyrrolidine, azetidine, tetrahydrofuran, and N-oxide derivatives of heterocyles containing basic nitrogen. Any fused combinations of any of these above-defined heterocyclic rings is also a part of this definition. Attached to the heterocyclic ring can be substituents such as alkyls, amines, or halogens (F, Cl, Br, I).

The term alkyl is intended to include branched, cyclic and straight chain saturated aliphatic hydrocarbon groups having 1 to 15 carbon atoms, unless otherwise defined. Preferred straight or branched alkyl groups include methyl, ethyl, propyl, isopropyl, butyl, t-butyl and the like. Preferred cycloalkyl groups include cyclopentyl and cyclohexyl.

The term alkoxy represents an alkyl group of indicated carbon atoms attached through an oxygen linkage.

The term alkylamino represents an alkyl group of indicated carbon atoms attached through a nitrogen atom linkage.

The term dialkylamino represents two alkyl groups of indicated carbon atoms attached through a nitrogen atom linkage.

The term small alkyl is intended to indicate those alkyls with C1 to C6 carbon atoms, either branched or linear in connection.

The term halo as used herein, represents fluoro, chloro, bromo or iodo.

The term aryl refers to aromatic rings e.g., phenyl, substituted phenyl and the like groups as well as rings which are fused e.g., naphthyl and the like. Aryl thus contains at least one ring having at least 6 atoms, with up to two such rings being present, containing up to 10 atoms therein, with alternating (resonating) double bonds between adjacent carbon atoms. The preferred aryl groups are phenyl and naphthyl. Aryl groups may likewise be substituted with 1–3 groups such as alkyl, halo, carboxyalkyl, alkylamino, dialkylamino, alkoxy, alkoxyamino and the like.

The term heteroaryl refers to a monocyclic aromatic hydrocarbon group having 5 or 6 ring atoms, or a bicyclic aromatic group having 8 to 10 atoms, containing at least one heteroatom, O, S, or N, in which a carbon or nitrogen atom is the point of attachment, and in which one additional carbon atom is optionally replaced by a heteroatom selected from O or S, an in which from 1 to 3 additional carbon atoms are optionally replaced by nitrogen heteroatoms. The heteroaryl group is optionally substituted with up to three groups. Heteroaryl thus includes aromatic and partially aromatic groups which contain one or more heteroatoms. Examples of this type are pyrrol, pyridine, oxazole, thiazole and oxazine. Additional nitrogen atoms may be present together with the first nitrogen and oxygen or sulfur, e.g., thiadizaole.

A preferred embodiment of the novel compounds of this invention is realized when, $R_1$–$R_4$ are independently H, alkyl, or halo;

A is alkyl, alkoxyamino, N, C=O, =O, or carboxyalkyl;

E is H, alkyl, aryl, heteroaryl, heterocycle, alkylamino, or dialkylamino; and

Y is H, alkyl, or halo.

The pharmaceutically acceptable salts of the compounds of formula I include the conventional non-toxic salts or the quaternary ammonium salts of the compounds of formula I formed e.g. from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The compounds of the present invention may have asymmetric centers and occur as racemates, racemic mixtures, and as individual diastereomers, with all possible isomers, including optical isomers, being included in the present invention.

Non-limiting examples of the novel compounds of this invention are as follows:

1,3-dihydro-1-{1-[4-oxo-cyclohex-1-yl]piperidin-4-yl}-2H-benzimidazol-2-one;

5-methyl-1,3-dihydro-1-{1-[4-oxo-cyclohex-1-yl]piperidin-4-yl}-2H-benzimidazol-2-one;

5-chloro-1,3-dihydro-1-{1-[4-oxo-cyclohex-1-yl]piperidin-4-yl}-2H-benzimidazol-2-one;

5-fluoro-1,3-dihydro-1-{1-[4-oxo-cyclohex-1-yl]piperidin-4-yl}-2-H-benzimidazol-2-one;

1,3-dihydro-1-{1-[2-fluoro-4-oxo-cyclohex-1-yl]piperidin-4-yl}-2-H-benzimidazol-2-one;

1,3-dihydro-1-{1-[2-oxo-1,3-dioxolan-5-yl]piperidin-4-yl}-2H-benzimidazol-2-one;

1,3-dihydro-1-{1-[2(1H)-oxo-tetrahydropyrimidin-5-yl]piperidin-4-yl}-2H-benzimidazol-2-one; and 1,3-dihydro-1-{1-[1,3-dimethyl-2(1H)-oxo-tetrahydropyrimidin-5-yl]piperidin-4-yl}-2H-benzimidazol-2-one.

The novel compounds of this invention are prepared by the following non-limiting procedures:

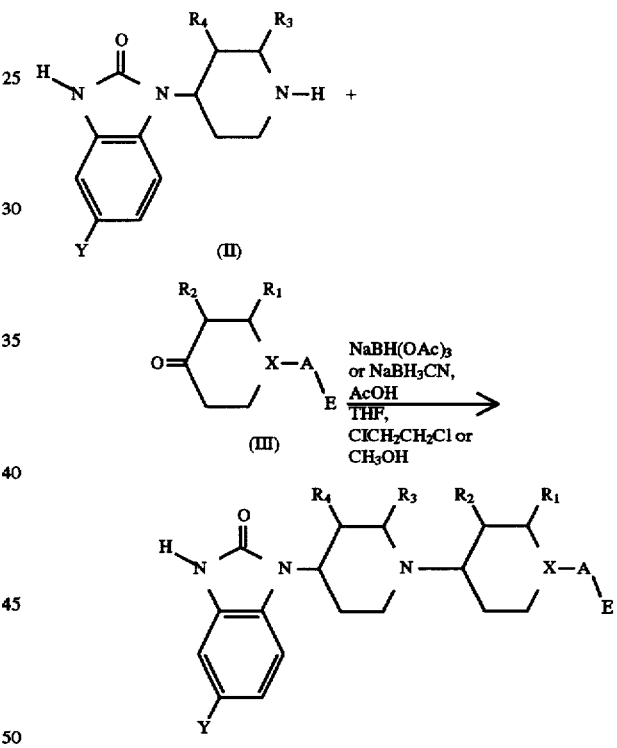

The reaction is carded out at room temperature (20°–30° C.) at a pH in the range of 2–7 (acidic) by the addition of glacial acetic acid or hydrochloric acid. For the preferred examples where X is C and A is =O, a suitably mono protected 1,4-cyclohexandione such as 1,4-cyclohexanedione mono-ethyleneketal can be used as an intermediate. Similarly, for examples where X is N a suitably protected 4-piperidone such as A-E is $CO_2Et$, $CO_2CH_2Ph$, or $CO_2C(CH_3)_3$ can be used as an intermediate. Deprotection by known methods (hydrogenation or acidic hydrolysis followed by basification) provides the free amine compound which can be acylated or alkylated by standard procedures. By this route the most preferred compounds can be obtained after isolation and purification.

The starting materials Compounds II and III are either commercially available or can be obtained by conventional procedures such as those described in the Examples section.

The selectivity of the compounds can be measured by radioligand displacement from m1–m5 receptors expressed in chinese hamster ovary cells (CHO) as described in the Examples section. The functional activity of the compounds can be assessed by measuring the agonist induced contractile response on muscle tissue from rabbit vas deferens (M1), the guinea pig left atria (M2), or the guinea pig ileum (M3) as described in the Examples section. The functional activity at the human muscarinic receptors can be assessed by measuring agonist induced phosphoinositide hydrolysis in CHO cells expressing the human m1 and m3 receptors or agonist inhibition of foskolin-stimulated adenylate cyclase activity in CHO cells expressing the human m2 receptor as described in the Examples section.

The instant compounds of this invention are useful in treating and/or preventing the development of glaucoma. Therapy to increase outflow can be administered by the use of the agent in eye drops. Indeed, in the vast majority of cases, treatment agents are administered to human eyes by the application of eye drops. Eye drops typically contain about 0.1% to 15% by weight of medicament, especially about 0.5 to 2% by weight of medicament, the remainder being comprised of carriers and other excipients well known in the art. A pH of about 4.5 to about 7.5 is expected to be acceptable as an ophthalmic drop and practical in terms of known solubility and stability of piperidine. Phosphate buffering is also common for eye drops and is compatible with the instant muscarinic agonist. A common regimen for application of eye drops is one to four times a day spaced evenly throughout waking hours. More effective agents may require fewer applications or enable the use of more dilute solutions.

The novel pharmaceutical formulations of this invention are also adapted for oral administration such as tablets, capsules and the like; for nasal administration, especially in the form of a spray; for injection, in the form of a sterile injectable liquid; or for topical ocular administration in the form of solutions, ointments, solid water soluble polymeric inserts, or gels.

The following example is provided in order that this invention might be more fully understood; it is not to be construed as limitative of the invention. The compounds are characterized analytically using techniques such as nuclear magnetic resonance, mass spectrometry, chromatography and the like.

EXAMPLE 1

1,3-Dihydro-1-{1-[4-oxocyclohex-1-yl]piperidin-4-yl}-2-H-benzimidazol-2-one

Step 1: A mixture of 5 g of 1,4-cyclohexanedione monoethyleneketal, 4.3 g of 1,3-dihydro-1-(4-piperidinyl)-benzimidazol-2H-one, 75 mL of 1,2-dichloroethane, 1.2 mL of acetic acid and 5.45 g of sodium triacetoxyborohydride was stirred at room temperature for 48 h. The reaction mixture was poured into 500 mL chloroform and 500 mL saturated aqueous $Na_2CO_3$ and the layers separated. The aqueous layer was extracted with 2×250 mL of chloroform and the combined organic layers dried over $MgSO_4$ and concentrated under reduced pressure. Trituration of the crude product with 200 mL of ethyl ether gave 7.0 g of the ethylene ketal of 1,3-dihydro-1-{1-[4-oxocyclohex-1-yl]piperidin-4-yl}-2H-benzimidazol-2-one as a white solid: mp=208°–210° C.; $^1$H NMR (400 MHz, $CDCl_3$) 9.14 (br s, 1H), 7.3 (m, 1H), 7.1 (m, 1H), 7.05 (m, 2H), 4.35 (br s, 1H), 3.96 (s, 4H), 3.05 (br d, J=6.6, 2H), 2.45 (m, 4H), 1.84 (br d, J=2.8, 5H), 1.72–1.55 (m, 6H).

Step 2: A mixture of 7.0 g of the ethylene ketal of 1,3-dihydro-1-{1-[4-oxocyclohex-1-yl]piperidin-4-yl}-2H-benzimidazol-2-one, 80 mL of glacial acetic acid, 80 mL of water and 20 mL of conc. HCl was heated under reflux for 2 h, then allowed to cool overnight. The mixture was concentrated under reduced pressure, diluted with 100 mL of saturated $Na_2CO_3$ and extracted into 3×200 mL of $CHCl_3$. The combined organic extracts were dried over $MgSO_4$ and concentrated under reduced pressure. Trituration with ether-ethyl acetate and drying under vacuum gave 5 g of 1,3-dihydro-1-{1-[4-oxocyclohex-1-yl]piperidin-4-yl}-2H-benzimidazol-2-one as a white solid: mp=221°–223° C.; $^1$H NMR (400 MHz, $CDCl_3$) 8.68 (br s, 1H), 7.28 (m, 2H), 7.07 (m, 2H), 4.35 (br s, 1H), 3.12 (br d, J=8.7, 2H), 2.82 (br t, J=9.74, 2H), 2.50 (br t, J=13.76, 2H), 2.44–2.32 (m, 6H), 2.06 (br s, 2H), 1.87 (br d, J=10.9, 4H). Analysis calculated for $C_{18}H_{23}N_3O_2 \cdot 0.4\ H_2O$: C: 67.44, H: 7.48, N: 13.11. found C: 67.44, H: 7.41, N: 12.86. The citrate salt was crystallized from ethyl acetate/methanol: $C_{18}H_{23}N_3O_2 \cdot 1.0\ H_2O \cdot 1.0\ C_6H_8O_7$: C: 55.06, H: 6.35, N: 8.03. found C: 55.35, H: 6.25, N: 7.89.

EXAMPLE 2

Radioligand Binding Studies

The affinity of muscarinic agonists for m1–m5 receptors expressed in chinese hamster ovary cells (CHO) were determined using the technique described by Dorje et al., J. Pharmacol. Exp. Ther. 256: 727–733 (1991).

When 80–100% confluent, CHO cells were harvested, and transferred to centrifuge robes containing CHO buffer (20 mM HEPES at pH 7.4 containing 5 mM $MgCl_2$). The cells were homogenized using a Brinkman Polytron homogenizer for 30 seconds at a setting of 5, on ice. The homogenate was centrifuged at 40,000×g for 15 minutes at 4° C. in a Beckman J2-21M centrifuge. The supernatant was discarded and the homogenization/centrifugation step repeated once. Pelleted membranes were resuspended in CHO buffer to a concentration of one flask harvested (75 $cm^2$) per mL of buffer, mixed well and aliquoted in cryovials (1 mL/vial). The vials were stored at −70° C. until used in the assay. The binding incubation was done in polypropylene macrowell tube strips in a final volume of 0.5 mL of HEPES buffer (20 mM; pH 7.4 containing 5 mM $MgCl_2$) containing 0.1 mL of cell membrane suspension, 3H-N-methylscopolamine (NEN Corporation, NET-636, 70–87 C/mmole) at a final concentration of approximately 0.2 nM and the competing drug in a varying range of concentrations or vehicle. After the addition of the cell homogenate the tubes were agitated on a vortex mixer and then placed in a water bath at 32° C. After 90 minutes of incubation, the membranes were harvested on a Skatron filtermat (#11734) or a Wallac filtermat (#205-404) using three washes of HEPES buffer (4° C.). The radioactivity on the filters was counted in a Packard 2200CA scintillation counter or in a Wallac 1205 Betaplate scintillation counter. Specific binding was defined as the difference in binding observed in the presence and absence of 10 micromolar atropine and accounted for at least 80% of total binding. $K_i$ values were calculated using the program LIGAND. Compounds displayed $K_i$ values at m1, m2 and m4 in the range of 1 nM to 5,000 nM. All compounds described herein displayed typically greater than 300-fold less potency at the m3 receptor subtype, in the range of 300 nM to 114,000 nM.

EXAMPLE 3 m2 receptor agonist activity on the guinea pig left atria

The technique described by Feifel et al., Brit. J. Pharmacol. 99: 455–460 (1990) was used as follows: Duncan-Hartley guinea pigs (Hazelton) weighing 300–600 g, are asphyxiated with $CO_2$. The abdomen is opened and the left atria is rapidly removed. The tissues are placed in a Petri dish containing oxygenated Krebs solution [NaCl, 118 mM; KCl, 4.7 mM; $CaCl_2$, 2.5 mM; $KH_2PO_4$, 1.2 mM; $MgSO_4$, 1.2 mM; $NaHCO_3$, 25 mM; dextrose, 11 mM] warmed to 37° C. Each atria is attached to platinum electrodes with 4–0 surgical silk and placed in a 10 mL jacketed tissue bath containing Krebs buffer at 37° C., bubbled with 5% $CO_2$/ 95% $O_2$. The tissues are connected to a Statham-Gould force transducer; 0.75 gram of tension is applied and the tissues are electrically stimulated. [EFS parameters are 3 Hz; 4 ms duration; voltage is set to 5 V.] The contractions are recorded on a Gould strip chart recorder. The tissues are washed every 20 minutes and allowed to equilibrate. A concentration response curve to the agonist is determined. Tissues are washed every 20 minutes for 60 minutes. The vehicle or compound is added to the bath and the tissues are incubated for 30 minutes. Agonist $EC_{50}$ values are determined for both vehicle and compound treated tissues before and after treatment. The compounds displayed $EC_{50}$ values at M2 in the range of 5 to 100 nM.

What is claimed is:

1. A compound of structural formula I

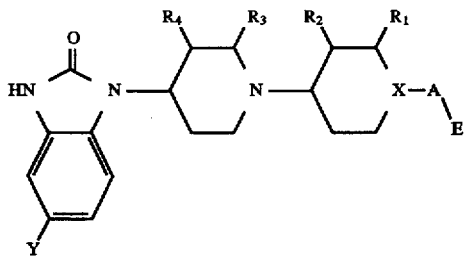

or pharmaceutically acceptable salts thereof, or diastereomers, enantiomers or mixtures thereof;
wherein:

$R_1$–$R_4$ are independently H, alkyl, halo, alkoxy, OH, HOCH2—, aryl, 3-pyridyl, 5-pyrimidinyl, amino, dialkylamino, alkene, thioalkyl, or alkylamino;

X is C;

A is alkyl, alkoxy, carboxyalkyl, alkoxyamino, alkylamino, dialkylamino, dialkoxyamino, carboxylic acid, =O, hydroxy, C=O, N, or does not exist;

E is H, alkyl, alkylamino, dialkylamino, aryl, heteroaryl, heterocycle, alkoxy, alkoxyaryl, alkoxyheteraryl, carbonyl heterocycle, alkoxyhetercycle, or does not exist; and Y is H, alkyl, halo, alkylamino, alkoxyamino, alkoxy, dialkylamino, or amino.

2. The compound of claim 1 wherein $R_1$–$R_4$ are independently H, alkyl, or halo; A is alkyl, alkoxyamino, N, C=O, =O, or carboxyalkyl; E is H, alkyl, aryl, heteroaryl, heterocycle, alkylamino, or dialkylamino; and Y is H, alkyl, or halo.

3. The compound:

1,3-dihydro-1-{1-[4-oxo-cyclohex-1-yl]piperidin-4-yl}-2H-benzimidazol -2-one;

5-methyl-1,3-dihydro-1-{1-[4-oxo-cyclohex-1-yl]piperidin-4-yl}-2H-benzimidazol-2-one;

5-chloro-1,3-dihydro-1-{1-[4-oxo-cyclohex-1-yl]piperidin-4-yl}-2H-benzimidazol-2-one;

5-fluoro-1,3-dihydro-1-{1-[4-oxo-cyclohex-1-yl]piperidin-4-yl}-2H-benzimidazol-2-one;

1,3-dihydro-1-{1-[2-fluoro-4-oxo-cyclohex-1-yl]piperidin-4-yl}-2H-benzimidazol-2-one;

1,3-dihydro-1-{1-[2-oxo-1,3-dioxolan-5-yl]piperidin-4-yl}-2H-benzimidazol-2-one;

1,3-dihydro-1-{1-[2(1H)-oxo-tetrahydropyrimidin-5-yl]piperidin-4-yl}-2H-benzimidazol-2-one; and 1,3-dihydro-1-{1-[1,3-dimethyl-2(1H)-oxo-tetrahydropyrimidin-5-yl]piperidin-4-yl}-2H-benzimidazol-2-one.

4. A method of treating ocular hypertension comprising topical ocular administration to a patient in need of such treatment of an effective ocular antihypertensive amount of a muscarinic agonist.

5. A method of treating ocular hypertension comprising topical ocular administration to a patient in need of such treatment of an effective ocular antihypertensive amount of a muscarinic agonist known to be selective for m2 receptors, but less active at m3 receptors.

6. A method of treating ocular hypertension comprising topical ocular administration to a patient in need of such treatment of an effective ocular antihypertensive amount of a compound of claim 1.

7. A method of treating ocular hypertension comprising topical ocular administration to a patient in need of such treatment of an effective ocular antihypertensive amount of a compound of claim 1, known to be selective for m2 receptors, but less active at m3 receptors.

8. A method of preventing ocular hypertension comprising topical ocular administration to a patient in need of such treatment of an effective ocular antihypertensive amount of a muscarinic agonist.

9. A method of preventing ocular hypertension comprising topical ocular administration to a patient in need of such treatment of an effective ocular antihypertensive amount of a muscarinic agonist known to be selective for m2 receptors, but less active at m3 receptors.

10. A method of preventing ocular hypertension comprising topical ocular administration to a patient in need of such treatment of an effective ocular antihypertensive amount of a compound of claim 1.

11. A method of preventing ocular hypertension comprising topical ocular administration to a patient in need of such treatment of an effective ocular antihypertensive amount of a compound of claim 1, known to be selective for m2 receptors, but less active at m3 receptors.

12. A composition useful for the treatment of ocular hypertension comprising an ophthalmologically acceptable carrier and an effective ocular antihypertensive amount of a muscarinic agonist.

13. A composition useful for the treatment of ocular hypertension comprising an ophthalmologically acceptable carrier and an effective ocular antihypertensive amount of a muscarinic agonist, known to be selective for m2 receptors, but less active at m3 receptors.

14. A composition useful for the treatment of ocular hypertension comprising an ophthalmologically acceptable carrier and an effective ocular antihypertensive amount of a compound of claim 1.

15. A composition useful for the treatment of ocular hypertension comprising an ophthalmologically acceptable carrier and an effective ocular antihypertensive amount of a compound of claim 1, known to be selective for m2 receptors, but less active at m3 receptors.

16. A composition useful for the prevention of ocular hypertension comprising an ophthalmologically acceptable carrier and an effective ocular antihypertensive amount of a muscarinic agonist.

17. A composition useful for the prevention of ocular hypertension comprising an ophthalmologically acceptable carrier and an effective ocular antihypertensive amount of a muscarinic agonist, known to be selective for m2 receptors, but less active at m3 receptors.

18. A composition useful for the prevention of ocular hypertension comprising an ophthalmologically acceptable carrier and an effective ocular antihypertensive amount of a compound of claim 1.

19. A composition useful for the prevention of ocular hypertension comprising an ophthalmologically acceptable carrier and an effective ocular antihypertensive amount of a compound of claim 1, known to be selective for m2 receptors, but less active at m3 receptors.

* * * * *